US009445622B2

(12) United States Patent
Petersen et al.

(10) Patent No.: US 9,445,622 B2
(45) Date of Patent: Sep. 20, 2016

(54) COMPOSITIONS AND METHODS FOR IMPROVING CREATINE SOLUBILITY AND STABILITY

(71) Applicants: Brent L. Petersen, Twin Falls, ID (US); Melinda Moss, Twin Falls, ID (US)

(72) Inventors: Brent L. Petersen, Twin Falls, ID (US); Melinda Moss, Twin Falls, ID (US)

(73) Assignee: Glanbia Nutritionals (Ireland) Ltd., Kilkenny (IE)

( * ) Notice: Subject to any disclaimer, the term of this patent is extended or adjusted under 35 U.S.C. 154(b) by 0 days.

(21) Appl. No.: 14/337,152

(22) Filed: Jul. 21, 2014

(65) Prior Publication Data

US 2014/0335257 A1 Nov. 13, 2014

Related U.S. Application Data

(63) Continuation-in-part of application No. 12/975,179, filed on Dec. 21, 2010.

(60) Provisional application No. 61/856,756, filed on Jul. 21, 2013, provisional application No. 61/288,767, filed on Dec. 21, 2009.

(51) Int. Cl.
A23L 2/39 (2006.01)
A23L 2/66 (2006.01)
A61K 9/10 (2006.01)
A61K 31/198 (2006.01)
A23L 1/305 (2006.01)
A61K 38/01 (2006.01)

(52) U.S. Cl.
CPC ............... *A23L 2/39* (2013.01); *A23L 1/3051* (2013.01); *A23L 1/3056* (2013.01); *A23L 2/66* (2013.01); *A61K 9/10* (2013.01); *A61K 31/198* (2013.01); *A61K 38/018* (2013.01); *A23V 2002/00* (2013.01)

(58) Field of Classification Search
None
See application file for complete search history.

(56) References Cited

U.S. PATENT DOCUMENTS

2007/0196508 A1* 8/2007 Heuer ....................... A23L 1/30
424/601
2009/0264363 A1* 10/2009 Ward ..................... A23L 1/3051
514/21.2

* cited by examiner

*Primary Examiner* — James H Alstrum Acevedo
*Assistant Examiner* — Roy Teller
(74) *Attorney, Agent, or Firm* — Donna J. Russell

(57) ABSTRACT

Disclosed are methods for improving nitrogenous acid (e.g., creatine) solubility, and products made by the method.

11 Claims, 3 Drawing Sheets

A

B

COMPOSITIONS AND METHODS FOR IMPROVING CREATINE SOLUBILITY AND STABILITY

This application is a non-provisional application claiming the benefit of priority of U.S. Provisional Patent Application No. 61/856,756, filed Jul. 21, 2013. This application is also a continuation-in-part of U.S. patent application Ser. No. 12/975,179, filed Dec. 21, 2010, which is a non-provisional which claimed the benefit of priority of U.S. Provisional Patent Application No. 61/288,767, filed Dec. 21, 2009.

FIELD OF THE INVENTION

The present invention relates to compositions and methods for increasing nitrogenous organic acid solubility. More specifically, the invention relates to methods for formulating products comprising amino acids and other nitrogenous organic acids in a more soluble form, and compositions made by such methods.

BACKGROUND OF THE INVENTION

Creatine (N-(aminoiminomethyl)-N-methyl glycine) is a nitrogenous organic acid which has a solubility of about 1 gram in 75 milliliters of water (about 13.3 g/L). Creatine has become one of the most popular supplements available in the sports nutrition market. In its solid form, creatine monohydrate powder is very stable, showing no signs of degradation over years, even at elevated temperatures. However, its use in liquid formulations, such as sports nutrition drinks, for example, has been limited by its low solubility and its decreased stability in solution. Creatine solubility may be increased at lower pH and higher temperatures, but at lower pH and at higher temperatures, creatine rapidly self-cyclizes into creatinine.

About 95% of the creatine in the human body is found in the muscle tissue. Because creatine plays a significant role in muscle metabolism, it is a popular supplement for athletes. It has also been suggested to have beneficial effects for disease conditions such as heart disease, chronic obstructive pulmonary disease (COPD), and Parkinson's disease.

One attempt to make a more soluble form of creatine has been described in U.S. Patent Publication Number 2011/0251280A1 (J. Owoc, now U.S. Pat. No. 8,445,466), which discloses the synthesis of amide-protected creatine molecules, generally formed by synthesizing peptides such as creatyl-L-glutamine.

Powdered drink mix sales have reached approximately one billion dollars per year. Their attractiveness is due, in part, because they can be available to consumers in canister-type containers, in single-shot sleeves, often referred to as "sticks," in cap-mounted delivery systems, or in tablet form, for example. In these forms, the mixes may be carried by the consumer in a pocket, purse, gym bag, briefcase, lunchbox, or even a pocket. Creatine has typically not been a suitable ingredient for many of these formulations because it is not sufficiently soluble to be readily mixed to form a solution from a powder mix. Therefore, what are needed are compositions and methods for providing creatine in a more soluble form.

SUMMARY OF THE INVENTION

The present invention relates to a method for improving creatine solubility, the method comprising admixing milled creatine with at least one protein component selected from the group consisting of peptides, polypeptides, proteins, and combinations thereof, to form a creatine/protein component composition wherein creatine comprises from about 10 to about 60 percent of the creatine/protein component composition; admixing the creatine/protein component composition into water at a pH of from about 2.0 to about 7.7 to give a creatine/protein component composition concentration in water of from about 5 to about 40 percent; and drying the creatine/protein component to provide a creatine-containing product with increased creatine solubility which can be used in dry beverage mixes.

In some aspects of the invention, the method may include co-acidifying creatine and at least one protein component to form an acidified creatine/protein composition, followed by drying the acidified creatine/protein composition to produce a composition comprising creatine in a more soluble form.

The invention also relates to a method comprising micronizing at least one nitrogenous organic acid, such as, for example, creatine, so that a nitrogenous organic acid product is formed wherein at least about 90% of the product comprises particle sizes of less than or equal to about 160 microns (i.e., about 160 microns or less); admixing the product with at least one protein component so that the nitrogenous organic acid product comprises from about 10 to about 60 percent of a solids mixture formed by the nitrogenous organic acid product and the at least one protein component; admixing the solids mixture with water to form a suspension wherein the solids mixture comprises from about 5 percent to about 40 percent of the suspension; and drying the suspension. In various aspects, the step of admixing the solids mixture with water further comprises blending the suspension to form a substantially homogeneous suspension; and the step of drying the suspension further comprises stirring the suspension during drying to maintain the homogeneous suspension during drying. Some aspects of the invention provide creatine as the at least one nitrogenous organic acid. In some aspects the at least one protein component comprises one or more whole proteins, one or more protein fragments (i.e., polypeptides), one or more peptides, or combinations thereof. In some aspects, the at least one protein is derived from whey protein, such as whey protein isolate or whey protein concentrate, for example. In some aspects, the protein component can comprise peptides from hydrolyzed whey protein.

The invention also relates to compositions made by the method, the compositions comprising nitrogenous organic acid products in a more soluble form. The inventors have found that this method of combining the steps of micronizing (e.g, milling) creatine, for example, followed by mixing the micronized creatine with hydrolyzed whey peptides to form a creatine/peptides composition, mixing the creatine/peptides composition in water, and drying the creatine/peptides composition after it has been hydrated by the water, produces a creatine-containing composition that provides creatine in a significantly more soluble form. The creatine-containing composition is ideal for ready-to-mix powdered drink mixes, for example.

DETAILED DESCRIPTION

Figure 1:
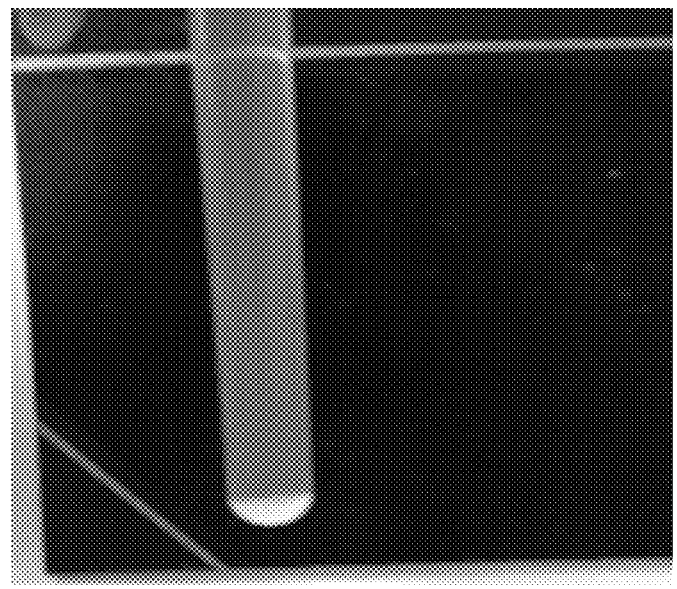
FIG. 1 illustrates the results of admixing into water (A) a composition comprising milled creatine admixed with a protein component and water, and (B) milled creatine admixed with a protein component, co-dried according to the method of the invention, then admixed with water.
Figure 1:
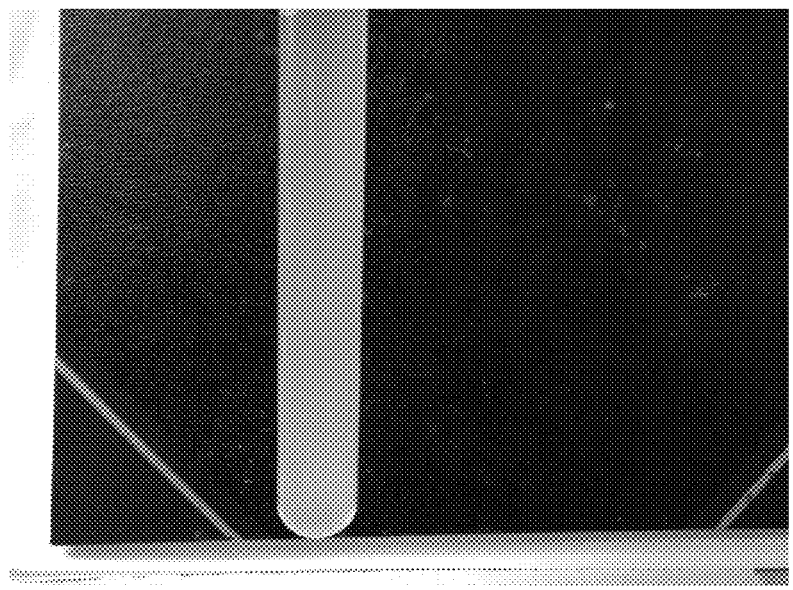

The inventors have developed a method for improving the solubility of a nitrogenous organic acid of limited solubility, such as creatine, for example, the method comprising admixing at least one milled nitrogenous organic acid, such as creatine, with at least one protein, wherein the term "protein" may include protein(s), polypeptides, peptides, or combinations thereof, and wherein the admixing may occur prior to or after admixing the nitrogenous organic acid and protein with water (i.e., admixing may involve powder/powder, powder/liquid, liquid/powder, or liquid/liquid components comprising the nitrogenous organic acid and protein, respectively), followed by co-drying the hydrated admixed nitrogenous organic acid and protein. For example, in the method of the invention as it may apply to the production of a creatine product, creatine is admixed with at least one protein selected from the group consisting of peptides, polypeptides, proteins, and combinations thereof, to form a creatine/protein composition wherein the creatine comprises from about 10 percent to about 60 percent; admixing the creatine/protein composition into water to give an aqueous creatine/protein composition having a creatine/protein composition concentration of from about 5 to about 40 percent; and drying the aqueous creatine/protein composition to provide a creatine product with increased solubility. Creatine in this form is suitable as an ingredient in powder mixes, for example, that can be provided to beverage and/or supplement formulators in ready-to-mix small or large batch quantities and/or to consumers in canisters, jars, sleeves, packets, tablets, etc. for admixing into water or other liquid, as desired.

Even more preferably, the invention relates to a method comprising micronizing at least one nitrogenous organic acid so that a product is formed wherein at least about 90% of the product comprises particle sizes of less than or equal to about 160 microns; admixing the product with at least one protein component so that the product comprises from about 10 to about 60 percent of a solids mixture formed by the nitrogenous organic acid product and the at least one protein component; admixing the solids mixture with water to form a suspension wherein the solids mixture comprises from about 5 percent to about 40 percent of the suspension; and drying the suspension. In various aspects, the step of admixing the solids mixture with water further comprises blending the suspension to form a substantially homogeneous suspension; and the step of drying the suspension further comprises stirring the suspension during drying to maintain the homogeneous suspension during drying. The inventors have determined that stirring, cooling quickly with agitation, etc., can maintain the crystals formed by the nitrogenous organic acid (e.g., creatine) and protein in a small enough size to facilitate drying and keep the crystals from clogging the lines during processing.

The invention also relates to compositions made by the method, the compositions comprising at least one nitrogenous organic acid, such as creatine, for example, in a more soluble form. The inventors have also found that these compositions can provide creatine in a form that is significantly more soluble in liquid formulations such as supplements and beverages. In some aspects, these supplements and beverages can be acidic. Creatine solubility is generally reported to be about 1 gram creatine in 75 milliliters of water (about 13.3 g/L). The method of the invention increases the solubility to at least about 16 g/L, which represents an increase of at least about 20 percent. At a level of less than or equal to about 4 grams of creatine in 100 milliliters of water, where the creatine product has been produced by the method of the invention, the product is not only soluble, but also produces an aqueous solution of excellent clarity.

"Protein," as used herein, is a composition of one or more proteins, protein fragments (e.g., polypeptides), and/or peptides in a substantially solid form, such as, for example, a powder. However, since the protein component will be admixed with creatine and suspended, it is within the scope of the invention to utilize protein in liquid, as well as in solid form. For example, protein solutions may be used. The inventors have discovered that "wet-blending" creatine and protein (i.e., admixing creatine and protein in the presence of water), then drying the blend, produces a higher-quality creatine product with increased solubility. The method of the invention can be applicable to other nitrogenous acids and/or amino acids, as well. Those of skill in the art will recognize that the term "water" is generally interpreted broadly to include water (i.e. aqueous liquids) which may include ingredients or acceptable impurities which do not negatively impact the hydration of the nitrogenous organic acid/protein component admixture or the solids percentages described herein.

In the method of the invention, micronized creatine is admixed with a protein component so that the creatine comprises from about 10 to about 60 percent of a solids mixture formed by the amino acid and the protein component. The protein component may comprise synthesized proteins and/or peptides, but it is advantageous to utilize isolated proteins, protein fragments, isolated peptides, and/or peptides obtained by hydrolyzing proteins from natural sources such as plant proteins and/or animal proteins. Especially useful proteins may be derived from milk, such as, for example, whey protein, whey protein concentrate, and/or whey protein isolate from bovine milk, and/or may be selected from the group consisting of soy, egg, vegetable, fish, wheat, rice, corn, fungal proteins, meat or other protein sources known to those of skill in the art, and combinations thereof. Whey protein concentrates, for example, are commercially available from a variety of sources, such as, for example, Avonlac™ from Glanbia Nutritionals, Monroe, Wis. Whey protein isolates may be obtained by methods known to those of skill in the art or may be purchased from commercial sources such as, for example, Glanbia Nutritionals, which produces Provon®. Milk protein concentrates and milk protein isolates such as the Solmiko® products from Glanbia Nutritionals, as well as Glanbia's BarGain®, which is a source of both whey and soy protein, also provide proteins which may be used to produce peptides for the composition and method of the invention. The inventors have demonstrated that peptide compositions formed of hydrolyzed whey proteins provide excellent results in the method of the invention.

The creatine/protein component is admixed with water to form a suspension wherein the creatine/protein component solids comprise from about 5 percent to about 40 percent of the suspension. The inventors have demonstrated that a creatine/protein component solids level of approximately 30 percent of the suspension provides excellent results. In various aspects, the range of the creatine/protein component solids may comprise sub-ranges included within the 5 percent to 40 percent range, such as, but not limited to, from about 5 percent to about 30 percent of the suspension, from 10 to about 40 percent, from about 15 to about 30 percent of the suspension, etc. The pH range may also comprise sub-ranges thereof, such as, but not limited to, from about 3.0 to about 6.0, from about 2.5 to about 3.5, etc. The suspension is blended to provide a substantially homogeneous suspension (i.e., as homogeneous as is practicable under standard processing conditions known to those of skill in the art). Blending/mixing may be accomplished by a variety of means, including but not limited to the use of one or more homogenizers, centrifugal pumps, high shear mixers, microfluidizers, static mixers, and agitator tanks or a combination thereof. The suspension is then dried, with the homogeneity of the suspension being maintained as much as possible during the drying process, to produce a final product that forms a dry powder.

The inventors have discovered that micronizing a nitrogenous organic acid of more limited solubility, such as creatine, then admixing it with a protein component to provide a creatine/protein component admixture, admixing into liquid the creatine/protein component admixture (i.e., hydrating the creatine/protein component admixture), then drying the admixture without allowing it to sit for a significant period of time produces a significantly higher quality/ higher solubility creatine product. Drying should preferably take place within about one hour after admixing/processing in order to produce an optimum product comprising a powder that will provide ready-to-mix creatine (or other nitrogenous acid) in a more soluble form. Preferably, drying will be performed in-line, so that the stream of liquid goes directly from the mixing step or the pasteurization step to the dryer, with a minimal number of additional steps in-between.

To provide a substantially homogeneous suspension, it is advisable to blend the suspension with shear. Optionally, a pasteurization step may be performed following blending. For the step of drying and by way of a non-limiting example, the following conditions may be used to achieve a good yield: 225° F. inlet temperature, 85° F. outlet temperature, pressure 3 bars (43.5 psi). Suitable equipment for drying may be obtained from a variety of commercial sources and such equipment may readily be identified by those of skill in the art. Drying conditions may be altered by those of skill in the art to accommodate the needs of the producer. For example, procedures for drying suspensions are described in the *Handbook of Industrial Drying* (Mujumdar, A. S., CRC Press (Taylor and Francis Group), Boca Raton, Fla., 2007). Suitable mixers include, for example, high shear batch mixers commercially available from a variety of sources such as Silverson Machines, Inc., East Longmeadow, Mass. For example, a mixer such as the Silverson Flashblend® mixer, which is adapted for mixing powders with liquid and forming homogeneous suspensions thereof, may be used.

Micronizing the at least one nitrogenous acid/amino acid may be performed using a Micronizer Jet Mill (Sturtevant, Inc., Hanover, Mass.), for example. Suitable micronizers are available from a variety of commercial sources and may be chosen by those of skill in the art for the particular conditions and batch sizes desired. It should be understood in the art that the terms "micronized" and "milled" may be used interchangeably when referring to amino acids and other nitrogenous organic acids, for example.

Where it is desirable that the protein comprise peptides having a higher concentration of leucine, such as for the production of products for use in performance nutrition for example, these may be obtained using the method described in United States Patent Application Publication Number US20090264363A1 (Ward, L. et al.). Using such peptides, it is therefore possible to produce a creatine formulation which also comprises significant amounts of L-leucine. Compositions made by the method of the invention may be used in, for example, ready-to-mix formulations comprising creatine and amino acids and/or amino acids blended with other ingredients, and in ready-to-drink formulations comprising creatine and amino acids and/or amino acids blended with other ingredients.

The method of the invention may also be used to produce an acidified creatine product, which may, for example, be useful as an ingredient in drink formulations such as ready-to-mix powders. To produce an acidified product, the method can comprise a first step of co-acidifying creatine and at least one protein component, and a second step of co-drying the acidified creatine and acidified protein component. While not intending to be bound by theory, the inventors believe that co-processing the creatine with at least one protein component, as described by the method of the invention, interferes with the intermolecular associations that result in cyclization of creatine to form creatinine. Processing creatine with at least one protein component, as provided by the method of the invention, results in a product which may be used to formulate liquid compositions having higher solids content.

Amino acid interactions with and within proteins have been described previously. For example, amino acid composition of proteins has been reported to affect disulfide bond formation, with weakly hydrophilic and aromatic amino acids being more common in the areas near disulfide bonds, while aliphatic and hydrophobic residues are less common Marques, J. F. R. et al., "Amino Acid Patterns around Disulfide Bonds," *Int. J. Mol. Sci.* 2010, 11, 4673-4686). Arginine, a hydrophilic amino acid, weakens hydrophobic interactions between IL-6 and phenyl-sepharose, improving protein elution in hydrophobic interaction chromatography (Tsumoto, K., et al., "Arginine improves protein elution in hydrophobic interaction chromatography: The cases of human interleukin-6 and activin-A." *Journal of Chromatography A*, 22 Jun. 2007, Vol. 1154 (1-2): 81-86). According to Ashokkumar et al., "[i]n the dairy industry, the stability of dairy proteins toward heat treatment is a major processing issue. Exposure of whey proteins to temperatures in excess of 70° C. causes denaturation, which in turn leads to protein aggregation through both hydrophobic interactions and the formation of intermolecular disulfide bonds" ("Sonication increases the heat stability of whey proteins," *J. Dairy Sci.* 92:5353-5356). Ashokkumar et al. utilize a combination of heat treatment and sonication to disrupt these aggregates. Those of skill in the art, given the disclosure herein, may therefore find multiple additional uses for products of the invention, as well.

It should be understood that the terms "consisting of" and "consisting essentially of" may be substituted for the term "comprising." The invention may be further described by means of the following non-limiting examples.

Examples

Acidified Product

A mixture of hydrolyzed whey protein isolate and creatine was formed, with the hydrolyzed whey protein isolate forming 60 percent of the mixture and creatine forming 40 percent. The solids mixture was dissolved in water, pH adjusted to 3.25, the solids content being approximately 30% of the solution. With pH adjustment to pH 3.25, an acidified creatine/WPI product was formed. The solution was dried, resulting in a powdered, acidified creatine/WPI product that could readily be resuspended in solution.

A mixture of hydrolyzed whey protein isolate and creatine was formed, with the hydrolyzed whey protein isolate forming 70 percent of the mixture and creatine forming 30 percent. The solids mixture was dissolved in water, pH adjusted to 3.0, the solids content being approximately 20% of the solution. With pH adjustment to 3.0, an acidified creatine/WPI product was formed. The solution was dried, resulting in a powdered, acidified creatine/WPI product that could readily be re-suspended in solution.

Creatine recovery was determined following a method derived from the method described in the *Journal of Pharmaceutical and Biomedical Analysis*, 29 (2002) 939-945, taking into account the presence of the protein/peptides.

Non-Acidified Product

A mixture of hydrolyzed whey protein isolate and creatine was formed, with the hydrolyzed whey protein isolate forming 80 percent of the mixture and creatine forming 20 percent. The solids mixture was dissolved in water, pH was unadjusted (pH 7.0-7.5), the solids content being approximately 10% of the solution. The solution was dried, resulting in a powdered, creatine/WPI product that could readily be resuspended in solution.

Figure 2:
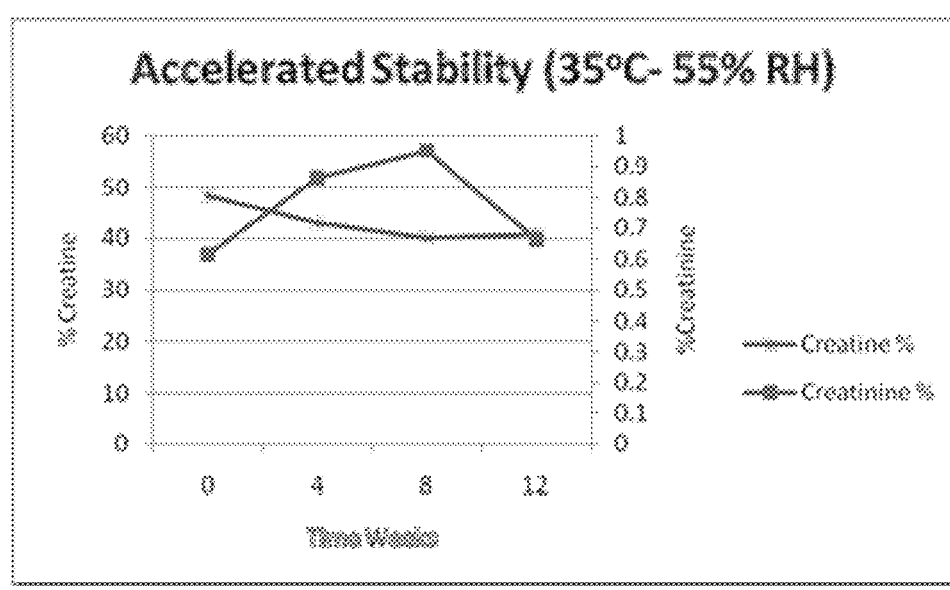
FIG. 2 is a graph illustrating the results of accelerated shelf-life testing of a creatine product made by the method of the invention. Percentages of creatine and creatinine were determined according to the method of Dash and Sawhney (Dash, A. K., et al. "A Simple LC Method with UV Detection for the Analysis of Creatine and Creatinine and Its Application to Several Creatine Formulations," *J. Pharm. Biomed. Anal.* (2002) 29(5): 939-945.) Percentage of creatine is indicated on the left Y-axis. Percentage of creatinine is indicated on the right Y-axis. Time (in weeks) is indicated on the X-axis. The creatinine degradation product remained at levels of less than 1% during the period of shelf-life testing.
Figure 3:
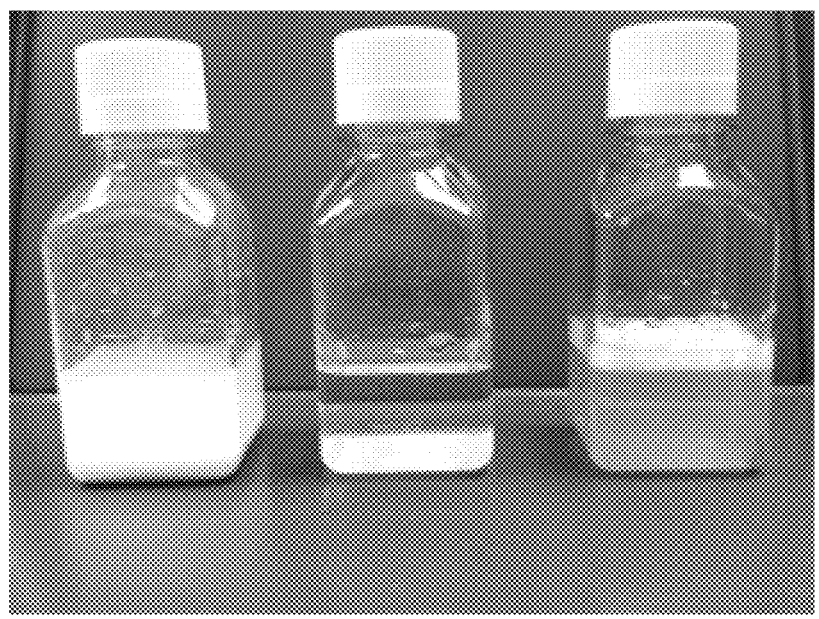
FIG. 3 is a photograph of three samples, illustrating the solubility—or lack thereof—of each. From left to right, the bottles contain 4 grams of micronized (i.e., milled) creatine admixed into water, 1.6 grams of milled creatine admixed into water, and 4 grams of a milled/co-dried creatine/protein product of the invention, containing 1.6 grams of milled creatine as a fraction of the 4 gram creatine/protein product.

The product was packaged in foil pouches and stored in a stability chamber for 12 weeks at 35° C. and 55% relative humidity. A single pouch was pulled at each time-point (every 4 weeks) and tested for creatine and creatinine following the method described by Dash and Sawhney. Creatine represented 42% of the powder by weight. Results are shown in FIG. 2. Due to some moisture loss during the processing, the initial creatine results tested artificially high, but the following time-points equilibrated at the target range. More importantly, the degradation product, creatinine, remained at acceptably low levels (<1%).

What is claimed is:

1. A method comprising admixing milled creatine with at least one protein component selected from the group consisting of peptides, polypeptides, proteins, and combinations thereof, to form a creatine/protein component composition wherein creatine comprises from about 10 to about 60 percent w/w of the creatine/protein component composition; admixing the creatine/protein component composition into water at a pH of from about 2.0 to about 7.7 to give a creatine/protein component composition concentration in water of from about 5 to about 40 percent w/v; and drying the creatine/protein component to provide a creatine-containing product with increased creatine solubility.

2. The method of claim 1 wherein the creatine-containing product is a powder.

3. The method of claim 1 wherein the step of admixing the creatine/protein component composition into water further comprises blending a creatine/protein suspension to form a substantially homogeneous suspension.

4. The method of claim 1 wherein the step of drying the creatine/protein component further comprises stirring a suspension, formed by the admixture of the creatine/protein component composition in water, during drying to maintain the homogeneous suspension during drying.

5. The method of claim 1 wherein the protein component comprises hydrolyzed whey protein.

6. The method of claim 1 wherein the milled creatine is micronized to form a creatine product wherein at least about 90% of the product comprises particle sizes of about 160 microns or less.

7. A product made by the process of micronizing creatine to form a creatine product wherein at least about 90% of the product comprises particle sizes of about 160 microns or less; admixing the product with at least one protein component so that the creatine product comprises from about 10 to about 60 percent w/w of a solids mixture formed by the creatine product and the at least one protein component; admixing the solids mixture with water to form a suspension wherein the solids mixture comprises from about 5 percent to about 40 percent w/v of the suspension; and drying the suspension to form a creatine-containing product.

8. The method of claim 7 wherein the creatine-containing product is a powder.

9. The method of claim 7 wherein the step of admixing the solids mixture with water further comprises blending a creatine/protein suspension to form a substantially homogeneous suspension.

10. The method of claim 7 wherein the step of drying the suspension further comprises stirring a suspension, formed by the admixture of the creatine/protein component composition in water, during drying to maintain the homogeneous suspension during drying.

11. The method of claim 7 wherein the protein component comprises hydrolyzed whey protein.

* * * * *